(12) United States Patent
Mardikian

(10) Patent No.: US 10,071,405 B2
(45) Date of Patent: Sep. 11, 2018

(54) APPARATUS FOR THERMAL TREATMENT OF ORGANIC WASTE

(71) Applicant: Albert Mardikian, Corona Del Mar, CA (US)

(72) Inventor: Albert Mardikian, Corona Del Mar, CA (US)

(*) Notice: Subject to any disclaimer, the term of this patent is extended or adjusted under 35 U.S.C. 154(b) by 274 days.

(21) Appl. No.: 15/001,091

(22) Filed: Jan. 19, 2016

(65) Prior Publication Data

US 2017/0203345 A1    Jul. 20, 2017

(51) Int. Cl.
*B09B 3/00* (2006.01)
*A61L 11/00* (2006.01)
*F26B 3/04* (2006.01)
*A61L 2/07* (2006.01)
*F26B 3/22* (2006.01)
*F26B 17/20* (2006.01)

(52) U.S. Cl.
CPC ............. *B09B 3/0091* (2013.01); *A61L 2/07* (2013.01); *A61L 11/00* (2013.01); *B09B 3/00* (2013.01); *F26B 3/04* (2013.01); *F26B 3/22* (2013.01); *F26B 17/20* (2013.01); *F26B 2200/02* (2013.01)

(58) Field of Classification Search
CPC .................................................... B09B 3/0091
See application file for complete search history.

(56) References Cited

U.S. PATENT DOCUMENTS

| 1,625,554 A | 4/1927 | Liggett |
| 1,813,750 A | 7/1931 | Mackenzie |
| 2,171,949 A | 9/1939 | Roca et al. |
| 2,609,993 A | 9/1952 | Planoil |
| 2,977,873 A | 4/1961 | Crane |
| 3,100,143 A | 8/1963 | Doggett |

(Continued)

FOREIGN PATENT DOCUMENTS

| EP | 0722486 A1 | 7/1996 |
| JP | S50158970 A | 12/1974 |

OTHER PUBLICATIONS

EffEnergy; BTU Values Mar. 2006.

(Continued)

*Primary Examiner* — Donald R Spamer
(74) *Attorney, Agent, or Firm* — Patent Law Agency, LLC; Peter Ganjian

(57) ABSTRACT

The present disclosure provides an apparatus for thermal treatment of a pre-defined amount of organic waste. The apparatus includes a plurality of chambers to receive the pre-defined amount of organic waste. Further, the apparatus includes a double wall to encapsulate each of the plurality of chambers. Furthermore, the apparatus includes an auger accommodated within the cylindrical hollow body of each of the plurality of chambers. Moreover, each of the plurality of chambers has a cylindrical hollow body. The cylindrical body has a first diameter of a first section and a second diameter of a second section. In addition, each of the plurality of chambers is connected in succession for a continuous movement of the pre-defined amount of organic waste along a longitudinal axis. Further, the plurality of chambers includes a feed material inlet and a processed material outlet attached at a second end of the plurality of chambers.

20 Claims, 12 Drawing Sheets

(56) References Cited

U.S. PATENT DOCUMENTS

| | | | |
|---|---|---|---|
| 3,407,510 | A | 10/1968 | Lewis et al. |
| 3,473,494 | A | 10/1969 | Siracusa |
| 3,506,414 | A | 4/1970 | Skendrovic |
| 3,563,399 | A | 2/1971 | Shivers |
| 3,707,070 | A | 12/1972 | Chaplin |
| 3,777,680 | A | 12/1973 | Eck |
| 3,817,259 | A | 6/1974 | Strasser et al. |
| 3,845,220 | A | 10/1974 | Suzuki |
| 3,945,575 | A | 3/1976 | Marsh |
| 3,979,104 | A * | 9/1976 | LaCoste ............... F16J 15/3464 251/214 |
| 4,026,426 | A | 5/1977 | Shivvers |
| 4,026,678 | A | 5/1977 | Livingston |
| 4,046,325 | A | 9/1977 | Tucsok et al. |
| 4,063,903 | A | 12/1977 | Beningson et al. |
| 4,151,959 | A | 5/1979 | Deister |
| 4,192,746 | A | 3/1980 | Arvanitakis |
| 4,217,061 | A | 8/1980 | Eiland et al. |
| 4,458,428 | A | 7/1984 | Saeman |
| 4,479,048 | A | 10/1984 | Kinoshita |
| 4,559,720 | A | 12/1985 | Marquardt |
| 4,565,124 | A | 1/1986 | Stautland et al. |
| 4,644,664 | A | 2/1987 | Bradshaw |
| 4,884,353 | A | 7/1989 | Houle |
| 4,922,989 | A | 5/1990 | Backlund |
| 5,001,975 | A | 3/1991 | Finden |
| 5,105,555 | A | 4/1992 | Nakagomi |
| 5,181,432 | A | 1/1993 | Allen |
| 5,387,267 | A | 2/1995 | Warf |
| 5,454,521 | A | 10/1995 | Frazier et al. |
| 5,570,517 | A | 11/1996 | Luker |
| 5,743,178 | A | 4/1998 | Babbini |
| 5,971,305 | A | 10/1999 | Davenport |
| 6,089,169 | A | 7/2000 | Comiskey |
| 6,692,544 | B1 | 2/2004 | Grillenzoni |
| 7,252,691 | B2 | 8/2007 | Philipson |
| 7,520,457 | B1 | 4/2009 | Poitras et al. |
| D609,042 | S | 2/2010 | Wilmsen |
| 7,993,048 | B1 | 8/2011 | Collette et al. |
| 8,043,505 | B2 | 10/2011 | Noguchi et al. |
| 8,714,467 | B2 | 5/2014 | Lucas et al. |
| 9,423,178 | B2 | 8/2016 | Mardikian |
| 2005/0274035 | A1 | 12/2005 | Beal et al. |
| 2006/0130353 | A1 | 6/2006 | Eloo |
| 2006/0288884 | A1 | 12/2006 | Babbini |
| 2007/0164139 | A1 | 7/2007 | Lipowski et al. |
| 2007/0221362 | A1 | 9/2007 | Stewart et al. |
| 2008/0233310 | A1 | 9/2008 | Fujita |
| 2009/0060779 | A1 | 3/2009 | Chambe et al. |
| 2009/0090282 | A1 | 4/2009 | Gold et al. |
| 2010/0043246 | A1 | 2/2010 | Smith |
| 2010/0163396 | A1 * | 7/2010 | Michalek ............... A61L 12/00 201/25 |
| 2010/0179315 | A1 | 7/2010 | Medoff |
| 2010/0281767 | A1 | 11/2010 | Zeeck |
| 2010/0293846 | A1 | 11/2010 | Shaffer |
| 2010/0300368 | A1 | 12/2010 | Myers et al. |
| 2010/0304439 | A1 | 12/2010 | Medoff |
| 2010/0304440 | A1 | 12/2010 | Medoff |
| 2011/0041390 | A1 | 2/2011 | Flick et al. |
| 2011/0248109 | A1 | 10/2011 | Lesar et al. |
| 2012/0245257 | A1 | 9/2012 | Fascio |
| 2012/0277329 | A1 * | 11/2012 | Galloway ............... C10G 2/30 518/704 |
| 2013/0029394 | A1 | 1/2013 | Toll et al. |
| 2013/0205613 | A1 | 8/2013 | Mardikian |
| 2013/0306763 | A1 | 11/2013 | Carmel |
| 2014/0061340 | A1 | 3/2014 | Castronovo |
| 2014/0076693 | A1 | 3/2014 | Pankoke |
| 2014/0217214 | A1 | 8/2014 | Peterson et al. |
| 2014/0223810 | A1 | 8/2014 | Nordin |
| 2014/0231560 | A1 | 8/2014 | Lucas et al. |
| 2014/0259895 | A1 | 9/2014 | Mason |
| 2015/0276312 | A1 | 10/2015 | Mardikian |

OTHER PUBLICATIONS

Jordan Reduction Solutions ; Twin Shaft Shredders; http://www.jordanreductionsolutions.com.
http://www.kunsheng.com.tw/equipments.html website.
"Pelletizing rather than refining" ; Sun & Wind Energy, Sep. 2010; pp. 242 to 246.
WO 2004/080704 A1 ; dated Sep. 23, 2004 ; Atlas-Stord Denmark A/S.
Keyway—Keyseat; Nov. 29, 2014 ; Avneesh Khanna.
IAC Publishing, LLC; 2017 ; How Does Humidity Affect Static Electricity.
File Hisotry of U.S. Appl. No. 14/242,453, filed Apr. 1, 2014; Mardikian; Includes JP 550158970A.
REGREEN1-2PCT; PCT/US2016/047221 ; Filed: Aug. 16, 2016; File History, ISR, and Opinion; WO 2017/127135—dated Jul. 27, 2017.
REGREEN1-3PCT; PCT/US2016/049311 ; Filed Aug. 29, 2016; File History, ISR, and Opinion; WO 2017/127137—dated Jul. 27, 2017.
REGREEN1-4PCT; PCT/US2016/051185 ; dated Sep. 10, 2016 ; File History, ISR, and Opinion; WP 2017/142592—dated Aug. 24, 2017.
REGREEN1-6PCT ; PCT/US2017/018513 ; Filed Feb. 17, 2017 ; File History, ISR, and Opinion ; WO2017/143293—dated Aug. 24, 2017.
WO 91/06816 A1 (AKT Consultants PTY Limited) May 16, 1991.
U.S. Appl. No. 15/001,082, filed Jan. 19, 2016; Office Action dated Jul. 10, 2018.

* cited by examiner

APPARATUS FOR THERMAL TREATMENT OF ORGANIC WASTE

INTRODUCTION

The present disclosure relates to a field of waste management. More specifically, the present disclosure relates to an apparatus for thermal treatment of organic waste.

Over the years, the amount of organic waste has increased sharply. This increase can be attributed to factors such as increased demand and production of livestock and agricultural produce, mismanagement of livestock and agricultural produce, lack of proper waste management resources and the like. The organic waste occupies large sections of land. With time, the organic waste is improperly decomposed and affects the soil quality, air quality and water resource present nearby. In addition, the organic waste is wet and carries bad odor and other harmful bacteria. This occupancy of organic waste has a negative psychological impact on the neighborhood. To overcome this, the organic waste is thermally treated.

There are numerous conventional systems for the thermal treatment of organic waste and, especially, for the thermal conversion of organic wastes into useful products by a process involving dehydration, roasting or baking and sterilization. In one of the conventional treatment methods, the organic waste obtained from municipal dump areas are commonly dewatered and subjected to some type of sterilization treatment involving heating and roasting.

These conventional systems for thermal treatment of organic waste have several disadvantages. In one of the prior arts, an apparatus for the thermal treatment of organic materials, especially organic waste is provided. It makes use of a horizontally elongated tank in which the waste is agitated in contact with a thermally conductive wall externally heated by the circulation of a hot gas. The hot gas is generated by injecting, into the space between this wall and an insulated wall, a combustion gas from a burner into which vapors released from the organic material are fed. This is done to ensure that vapors are fully burned within the burner.

In another prior art, an apparatus for drying organic and other waste materials such as industrial by products, agricultural and animal wastes, blood and manure. The apparatus includes a round, flat bottom substantially closed pan with a double-wall bottom and side forming a jacket and having a paddle-type agitator receives the material to be dried. Heat is provided by a gas-fired incinerator which preheats air that is admitted to the pan and then drawn into and combusted in the incinerator together with gases and moisture evolved from the material being dried. The incinerator's combustion products are passed through the pan jacket to heat the material that is dried and vented through a chimney.

In yet another prior art, the biomass is moved through a reactor tube in which all the gasification and/or liquefaction takes place. Preferably, char exits the biomass reactor tube and enters the combustion chamber where the char serves as fuel for combustion. The combustion chamber partially surrounds the reactor tube and is in direct thermal contact with the reactor tube such that heat from the combustion chamber passes through the reactor wall and directly heats the biomass within the reactor tube.

These prior arts have several disadvantages. The apparatus mentioned in these prior arts have lower efficiency levels. Further, these apparatus have high fuel consumption and increased energy costs associated with inefficient operation. In addition, these apparatus fail to accommodate materials with non-uniform initial moisture content. In addition, these apparatus requires large size of chambers for accommodating organic waste. This consequent space requirements poses difficulty in transporting, assembling and placing the apparatus in operation, particularly in remote locations. Another disadvantage of conventional apparatus is the evolution of vapors and gases which carries bad odors and even toxic substances which should not be discharged into the atmosphere. These apparatus are are generally complex, require much manpower and are thermally uneconomical. In light of the above stated discussion, there is a need for a method and system that overcomes the above stated disadvantages.

SUMMARY

In an aspect, the present disclosure provides an apparatus for thermal treatment of a pre-defined amount of organic waste. The apparatus includes a plurality of chambers to receive the pre-defined amount of organic waste. Further, the apparatus includes a double wall to encapsulate each of the plurality of chambers. Furthermore, the apparatus includes an auger accommodated within the cylindrical hollow body of each of the plurality of chambers. Moreover, each of the plurality of chambers has a cylindrical hollow body. The cylindrical body has a first diameter of a first section and a second diameter of a second section. In addition, each of the plurality of chambers is connected in succession for a continuous movement of the pre-defined amount of organic waste along a longitudinal axis. The second diameter is less than the first diameter. Further, the plurality of chambers includes a feed material inlet attached at a first end of the plurality of chambers. In addition, the plurality of chambers includes a processed material outlet attached at a second end of the plurality of chambers. The double wall is made of a solid sheet metal to encapsulate the pre-defined amount of dry steam present in each of the plurality of chambers. The auger is positioned parallel to the longitudinal axis of each of the plurality of chambers. Moreover, the auger includes a cylindrical shaft to collect the pre-determined amount of dry steam. The cylindrical shaft is a hollow shaft that has a first distal end and a second distal end. Further, the auger includes a motor shaft for a rotation of the auger inside the plurality of chambers. Furthermore, the auger includes a second dry steam inlet for collection of the pre-defined amount of dry steam inside the hollow shaft of the auger. In addition, the auger includes a plurality of hollow walled blades that has a progressively constant flighting thickness. The flighting thickness is measured from the first distal end to the second distal end of the cylindrical shaft, with orientation of a first section of a flighting complementary to a second section of a juxtaposed, next, subsequent flighting. Further, the plurality of hollow walled blades has a progressively constant flight height. The progressively constant flight height is constant due to a constant diameter of the cylindrical shaft from the first distal end to the second distal end of the auger. Moreover, the plurality of hollow walled blades has a progressively constant distance between each of the plurality of hollow walled blades. The progressively constant distance is constant from the first distal end to the second distal end.

In an embodiment of the present disclosure, the apparatus further includes a first dry steam inlet for injection of the pre-defined amount of dry steam to each of the plurality of chambers and the auger. The first dry steam inlet is positioned adjacent to a surface of the double wall on an axis perpendicular to the longitudinal axis of the plurality of chambers. The first steam inlet is associated with a manual valve to control injection of the pre-defined amount of dry steam inside each of the plurality of chambers and the auger.

In an embodiment of the present disclosure, the apparatus further includes a plurality of dry steam inlets to inlet the pre-defined amount of dry steam to each of the plurality of chambers. In addition, each of the plurality of dry steam inlets is positioned on the surface of the double wall substantially parallel along the longitudinal axis of the plurality of chambers. The plurality of dry steam inlets is connected to a hollow tube that has a pre-defined length. The pre-defined length of the hollow tube for a first chamber of the plurality of chambers is measured from a base of a first chamber to a mid-point of the first chamber.

In an embodiment of the present disclosure, the apparatus further includes one or more bellow valves for removal of a collected cold steam. Moreover, each of the one or more bellow valves has a flow passage of generally a circular cross-section parallel substantially along the longitudinal axis. In addition, a valve disc member is positioned in the passage and has an outer periphery adapted to close the passage when rotated to a position generally transverse to the longitudinal axis.

In an embodiment of the present disclosure, the auger further includes a motor connected to the motor shaft for rotation of the cylindrical shaft and the plurality of hollow walled blades. The motor shaft has an interlocking element substantially aligned along the longitudinal axis of the auger. In addition, the motor shaft interlocks at the second distal end of the cylindrical shaft of the auger.

In another embodiment of the present disclosure, the motor rotates the auger at a pre-defined range of a speed of rotation.

In an embodiment of the present disclosure, the auger further includes a cold steam outlet for collection of the cold steam from the cylindrical shaft of the auger. The cold steam outlet is placed on a cross-sectional surface at the second distal end of the auger. The cold steam outlet is associated with an outlet valve to control the ejection of the cold steam out of the hollow shaft of the auger.

In an embodiment of the present disclosure, the apparatus further includes a second dry steam inlet that is placed on a cross-sectional surface at the first distal end of the auger. The second dry steam inlet is associated with an inlet valve for control of an injection of the pre-defined amount of dry steam inside the hollow shaft of the auger.

In an embodiment of the present disclosure, the feed material inlet has a feed inlet section aligned perpendicular to the longitudinal axis. In addition, the feed material inlet has a feed discharge section aligned perpendicular to the longitudinal axis of the plurality of chambers. The feed discharge section internally connected to the first chamber of the plurality of chambers.

In an embodiment of the present disclosure, the auger is an eccentric auger and a symmetric auger. In addition, the cylindrical shaft of the auger has a length measured between the first distal length and the second distal length.

In an embodiment of the present disclosure, the pre-defined amount of organic waste is thermally treated at a pre-determined temperature in the first chamber of the plurality of chambers.

In an embodiment of the present disclosure, the cylindrical shaft and the plurality of hollow walled blades of the auger includes a plurality of holes. The cylindrical shaft and the plurality of hollow walled blades are filled with the pre-defined amount of dry steam. The plurality of holes transfers jets of the pre-defined amount of dry steam to the pre-defined amount of organic waste present in the plurality of chambers.

In an embodiment of the present disclosure, the cylindrical shaft and the plurality of hollow walled blades are filled with the pre-defined amount of dry steam. In addition, an outer surface of the cylindrical shaft and the plurality of hollow walled blades transfer thermal energy to the pre-defined amount of organic waste through dissipation.

In an embodiment of the present disclosure, the cylindrical shaft and the plurality of hollow walled blades traverse from the first distal end to the second distal end along the longitudinal axis. In addition, the cylindrical hollow body of each of the plurality of chambers creates pressure for the pre-defined amount of organic waste that moves with the auger.

In an embodiment of the present disclosure, the cold steam collected from the cold steam outlet of the auger is fed back to a steamer for regeneration of the pre-defined amount of dry steam.

In another aspect, the present disclosure provides an apparatus for thermal treatment of a pre-defined amount of organic waste. The apparatus includes a plurality of chambers to receive the pre-defined amount of organic waste. Further, the apparatus includes a double wall to encapsulate each of the plurality of chambers. Furthermore, the apparatus includes an auger accommodated within the cylindrical hollow body of each of the plurality of chambers. Moreover, each of the plurality of chambers has a cylindrical hollow body. The cylindrical body has a first diameter of a first section and a second diameter of a second section. In addition, each of the plurality of chambers is connected in succession for a continuous movement of the pre-defined amount of organic waste along a longitudinal axis. The second diameter is less than the first diameter. Further, the plurality of chambers includes a feed material inlet attached at a first end of the plurality of chambers. In addition, the plurality of chambers includes a processed material outlet attached at a second end of the plurality of chambers. The double wall is made of a solid sheet metal to encapsulate the pre-defined amount of dry steam present in each of the plurality of chambers. Further, the auger includes a plurality of holes. The auger is filled with the pre-defined amount of dry steam. The plurality of holes transfers jets of the pre-defined amount of dry steam to the pre-defined amount of organic waste present in the plurality of chambers. Moreover, the auger includes a cylindrical shaft to collect the pre-determined amount of dry steam. The cylindrical shaft is a hollow shaft that has a first distal end and a second distal end. Further, the auger includes a motor shaft for a rotation of the auger inside the plurality of chambers. Furthermore, the auger includes a second dry steam inlet for collection of the pre-defined amount of dry steam inside the hollow shaft of the auger. In addition, the auger includes a plurality of hollow walled blades that has a progressively constant flighting thickness. The flighting thickness is measured from the first distal end to the second distal end of the cylindrical shaft, with orientation of a first section of a flighting complementary to a second section of a juxtaposed, next, subsequent flighting. Further, the plurality of hollow walled blades has a progressively constant flight height. The progressively constant flight height is constant due to a constant diameter of the cylindrical shaft from the first distal end to the second distal end of the auger. Moreover, the plurality of hollow walled blades has a progressively constant distance between each of the plurality of hollow walled blades. The progressively constant distance is constant from the first distal end to the second distal end.

In an embodiment of the present disclosure, the apparatus further includes a first dry steam inlet for injection of the pre-defined amount of dry steam to each of the plurality of chambers and the auger. The first dry steam inlet is positioned adjacent to a surface of the double wall on an axis perpendicular to the longitudinal axis of the plurality of chambers. The first steam inlet is associated with a manual valve to control injection of the pre-defined amount of dry steam inside each of the plurality of chambers and the auger.

In an embodiment of the present disclosure, the apparatus further includes a plurality of dry steam inlets to inlet the pre-defined amount of dry steam to each of the plurality of chambers. In addition, each of the plurality of dry steam inlets is positioned on the surface of the double wall substantially parallel along the longitudinal axis of the plurality of chambers. The plurality of dry steam inlets is connected to a hollow tube having a pre-defined length. The pre-defined length of the hollow tube for a first chamber of the plurality of chambers is measured from a base of a first chamber to a mid-point of the first chamber.

In an embodiment of the present disclosure, the apparatus further includes one or more bellow valves for removal of a collected cold steam. Moreover, each of the one or more bellow valves has a flow passage of generally a circular cross-section parallel substantially along the longitudinal axis. In addition, a valve disc member is positioned in the passage and has an outer periphery adapted to close the passage when rotated to a position generally transverse to the longitudinal axis.

In an embodiment of the present disclosure, the auger further includes a cold steam outlet for collection of the cold steam from the cylindrical shaft of the auger. The cold steam outlet is placed on a cross-sectional surface at the second distal end of the auger. The cold steam outlet is associated with an outlet valve to control the ejection of the cold steam out of the hollow shaft of the auger.

BRIEF DESCRIPTION OF THE DRAWINGS

Figure 1A:
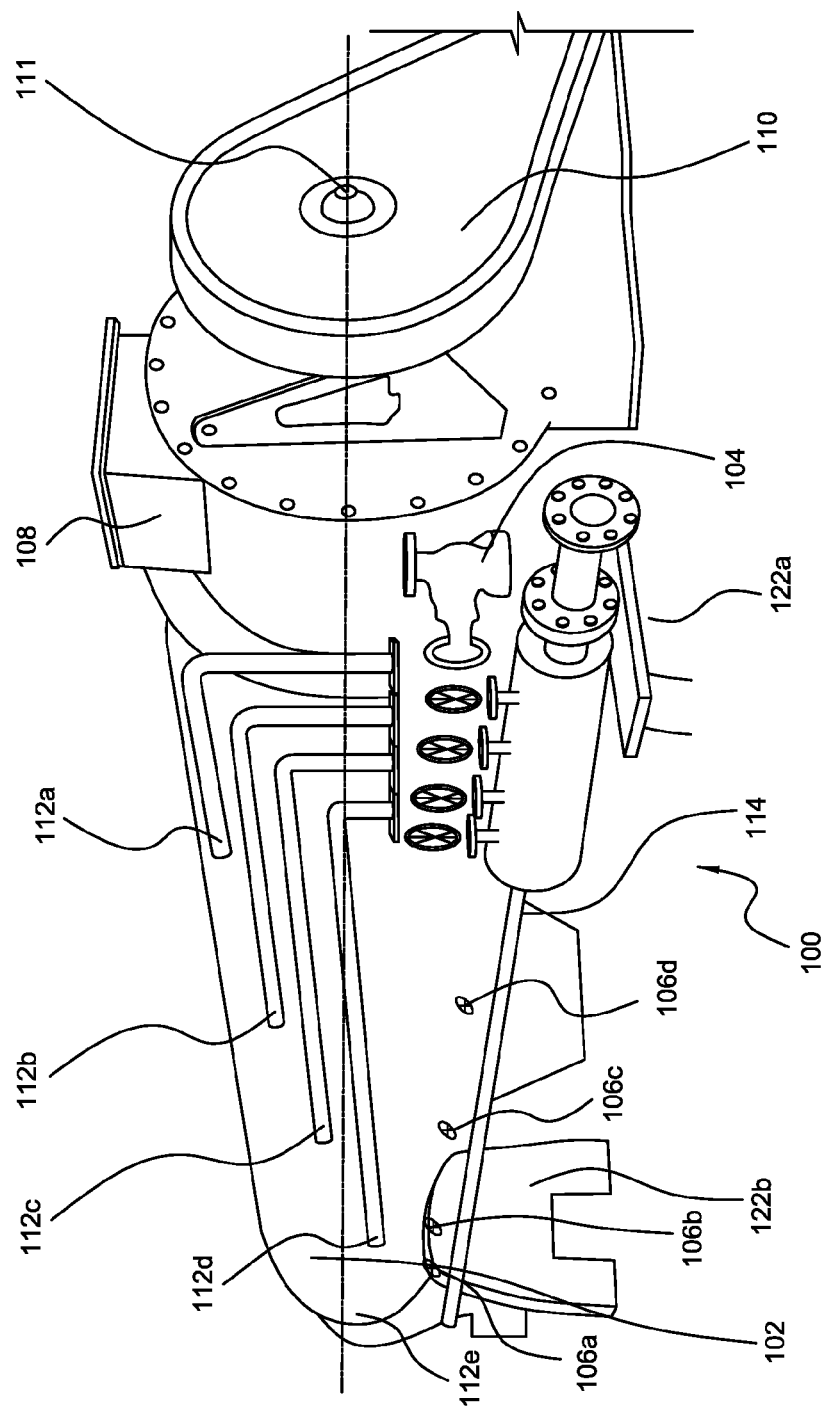
Figure 1B:
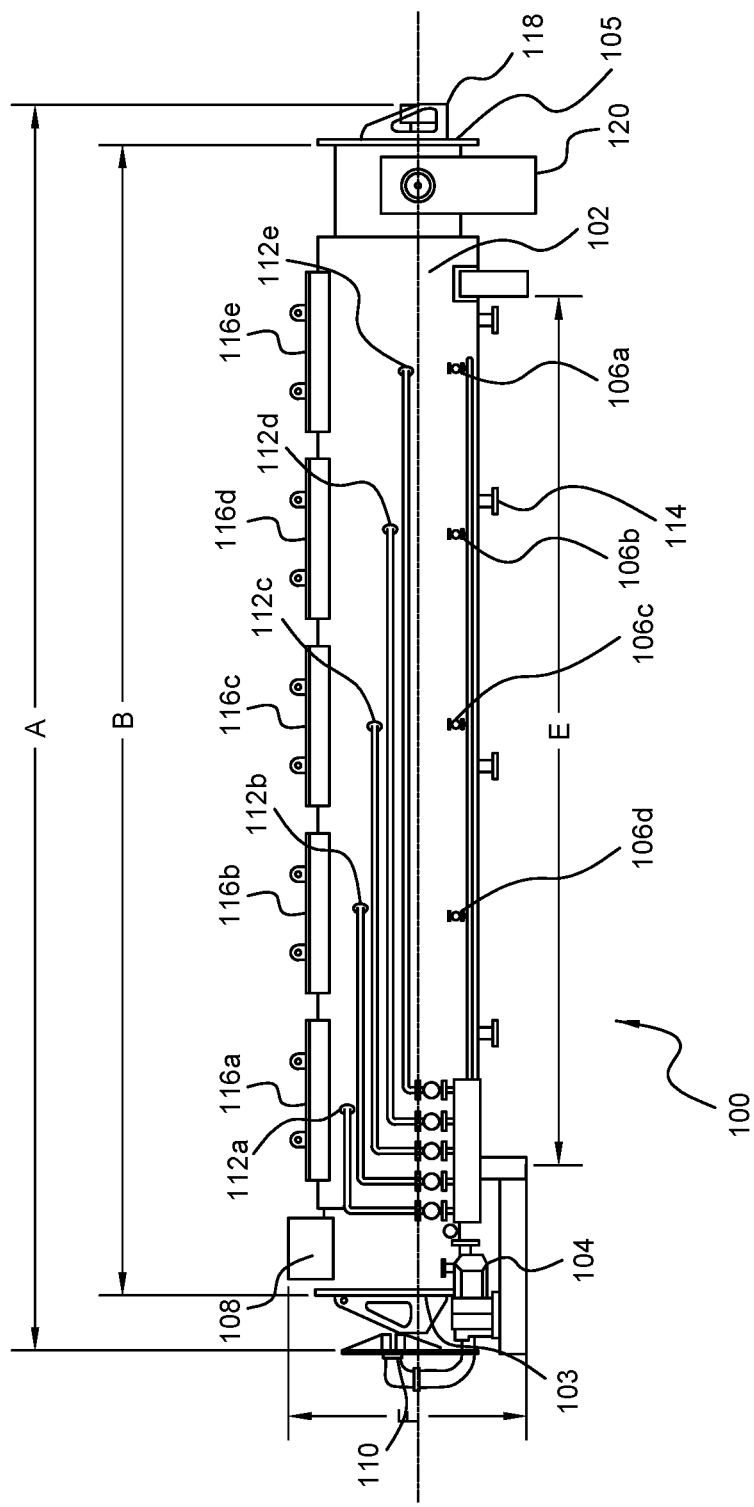
Figure 1C:
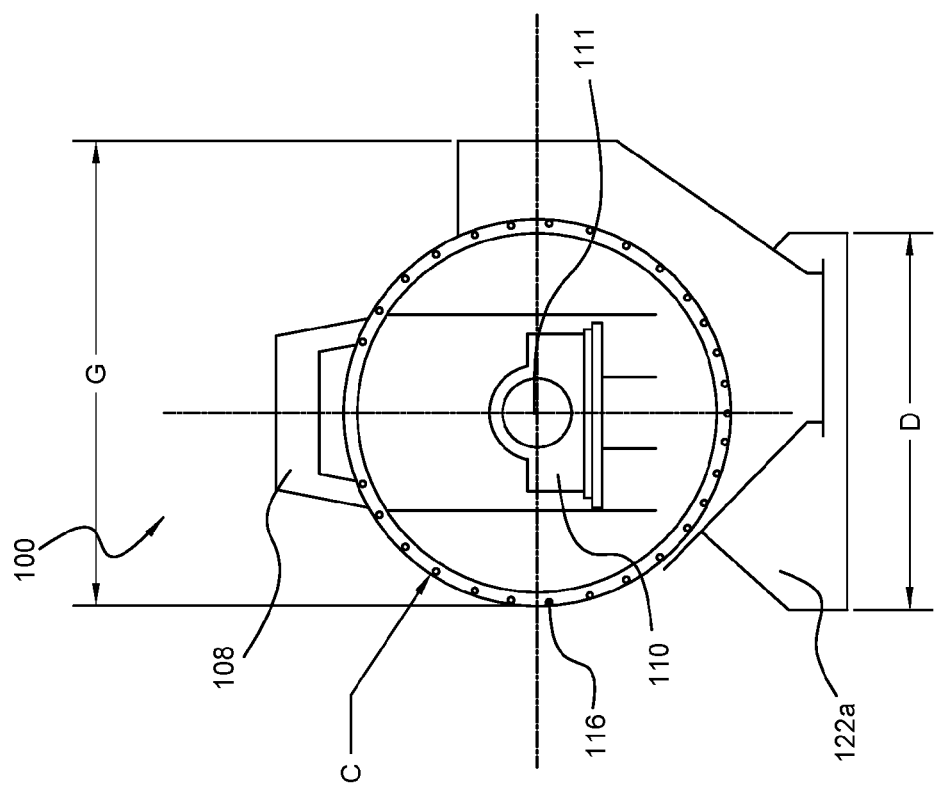
Figure 1D:
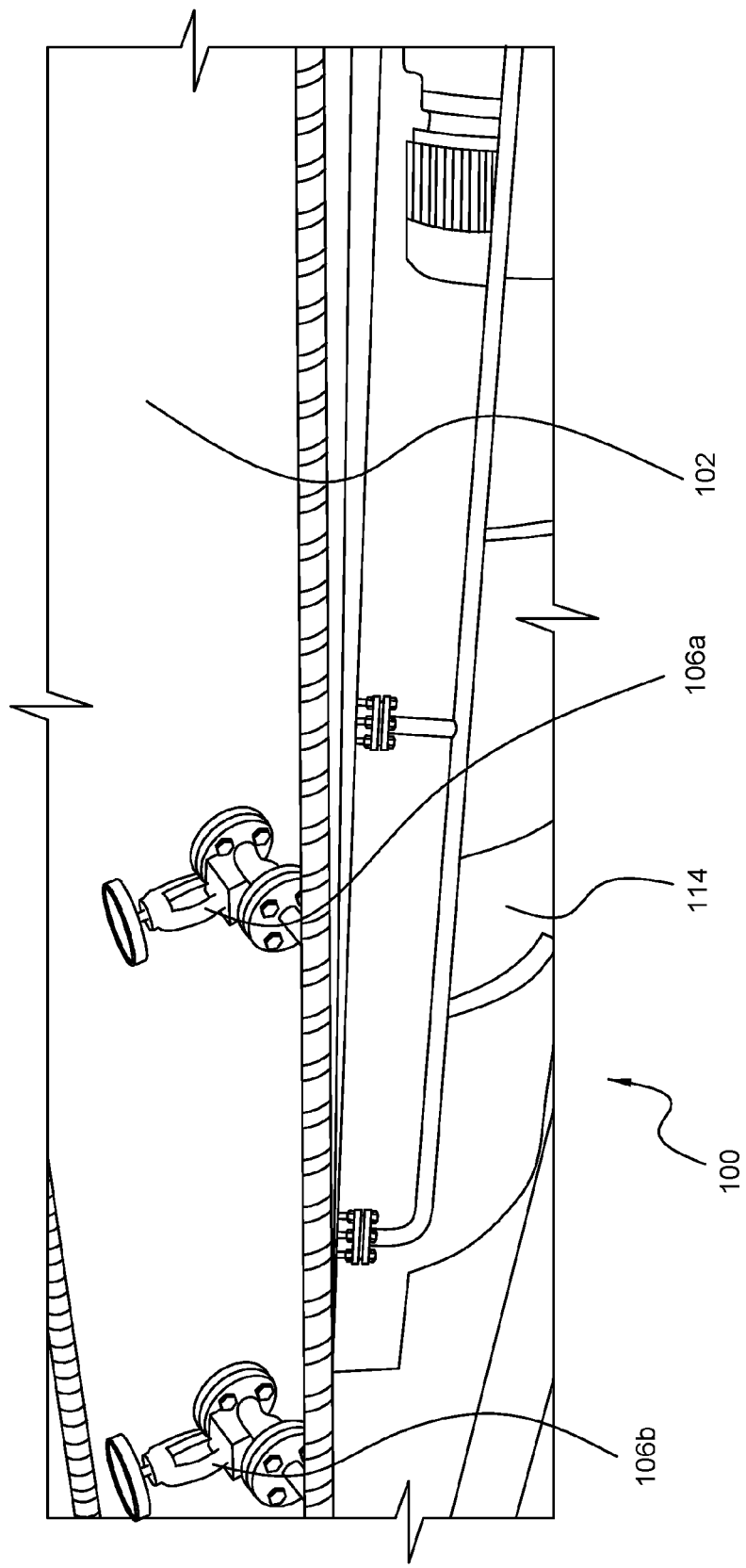
Figure 1E:
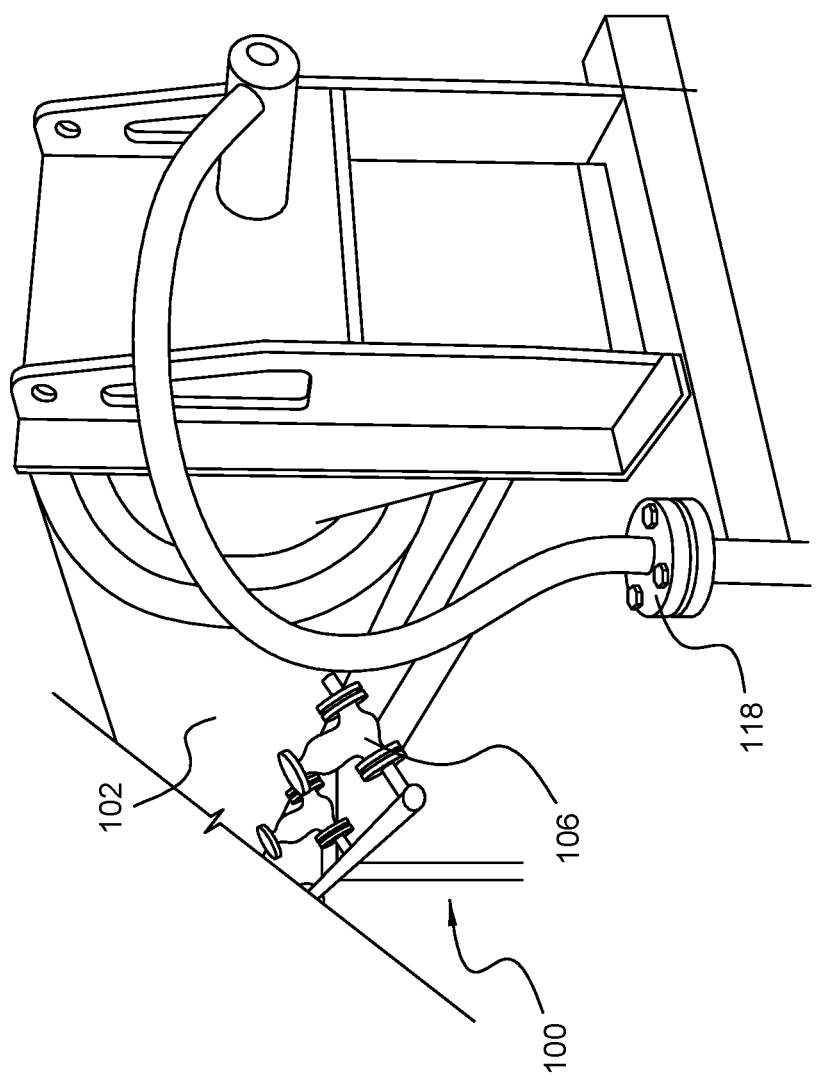
Figure 2A:
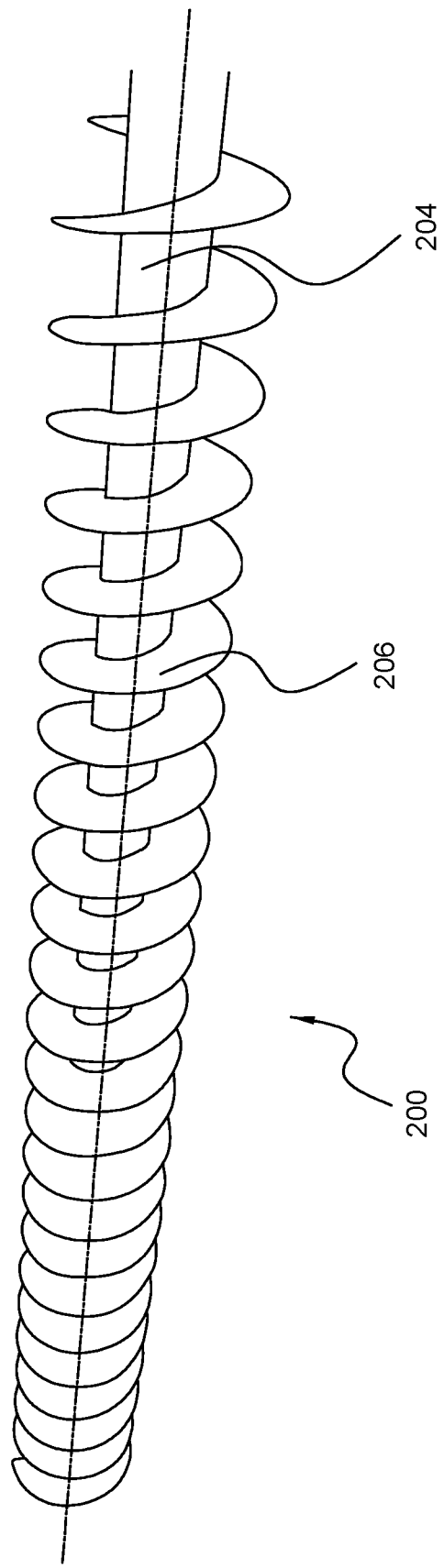
Figure 2B:
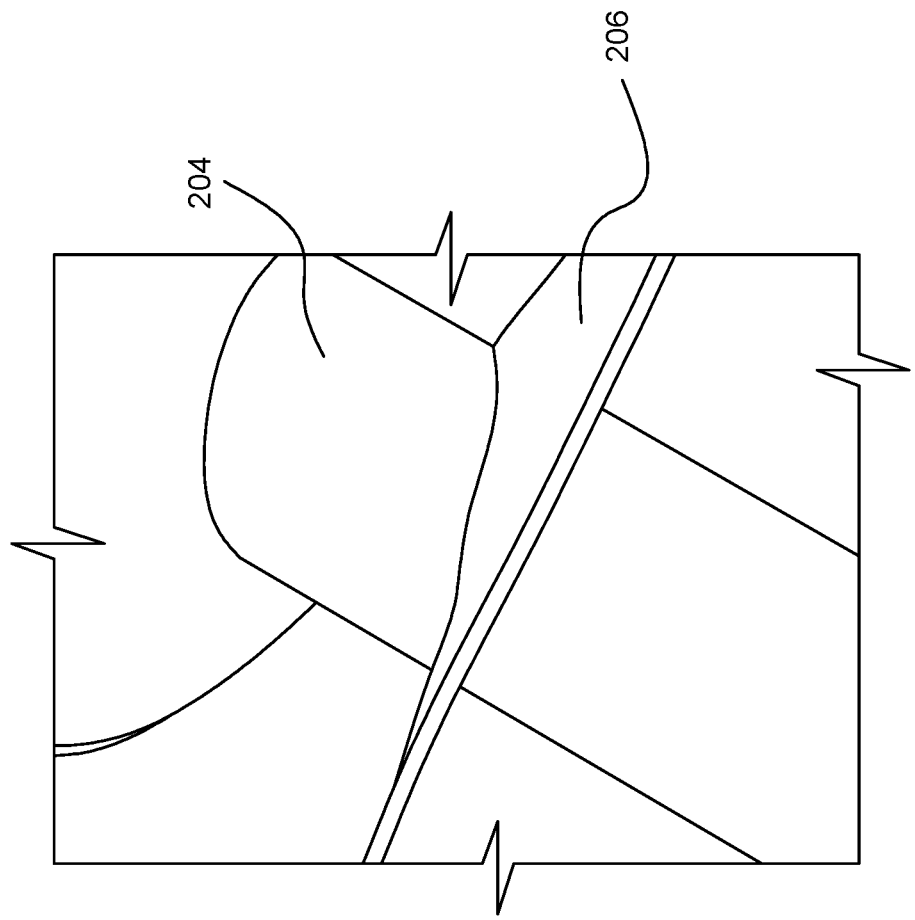
Figure 2C:
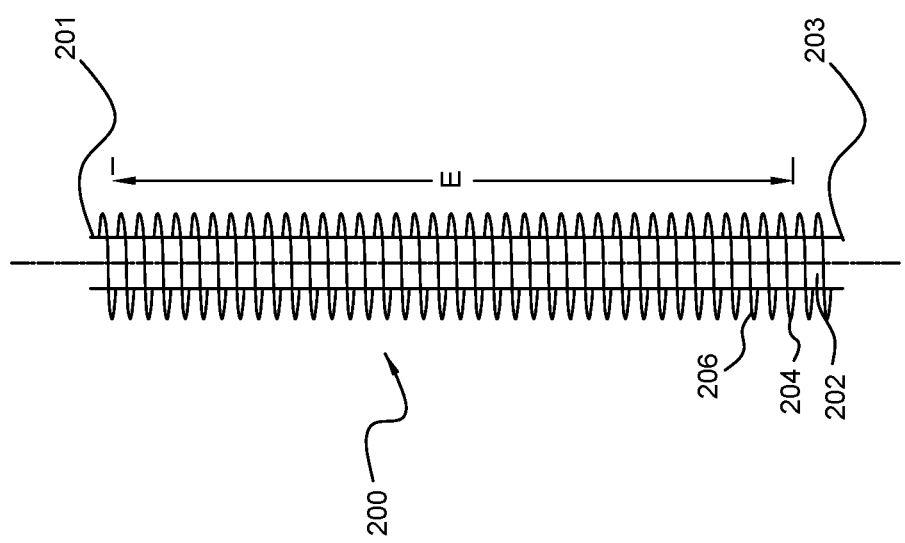
Figure 2D:
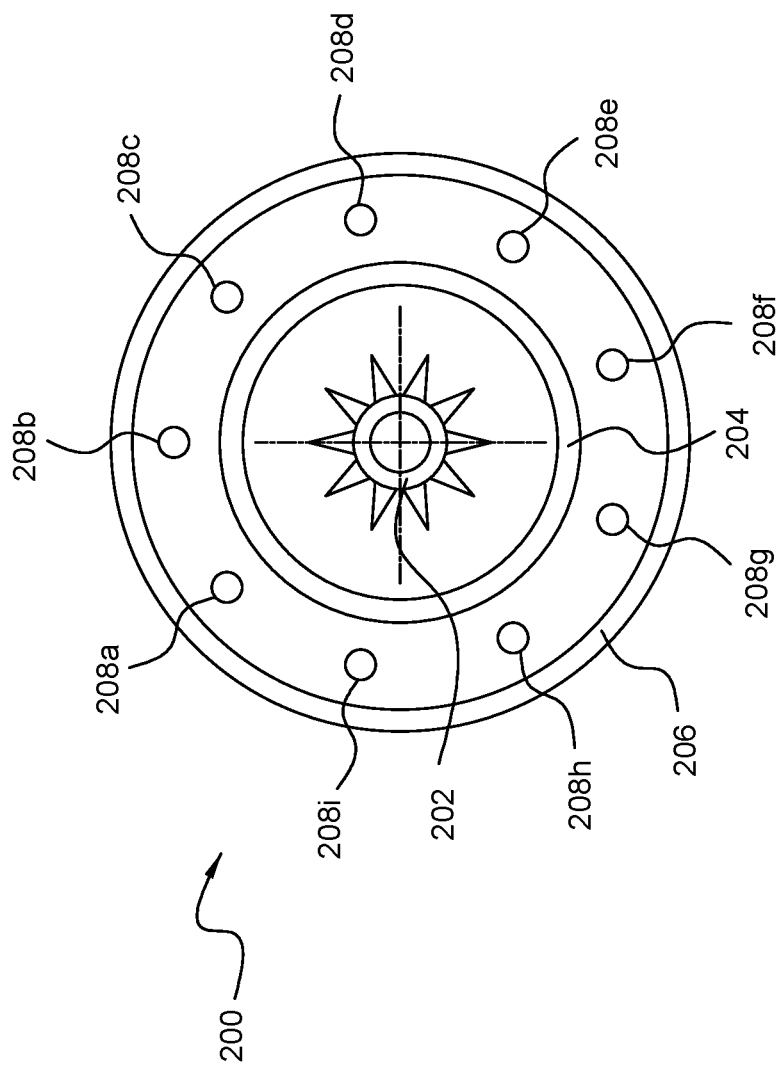
Figure 2E:
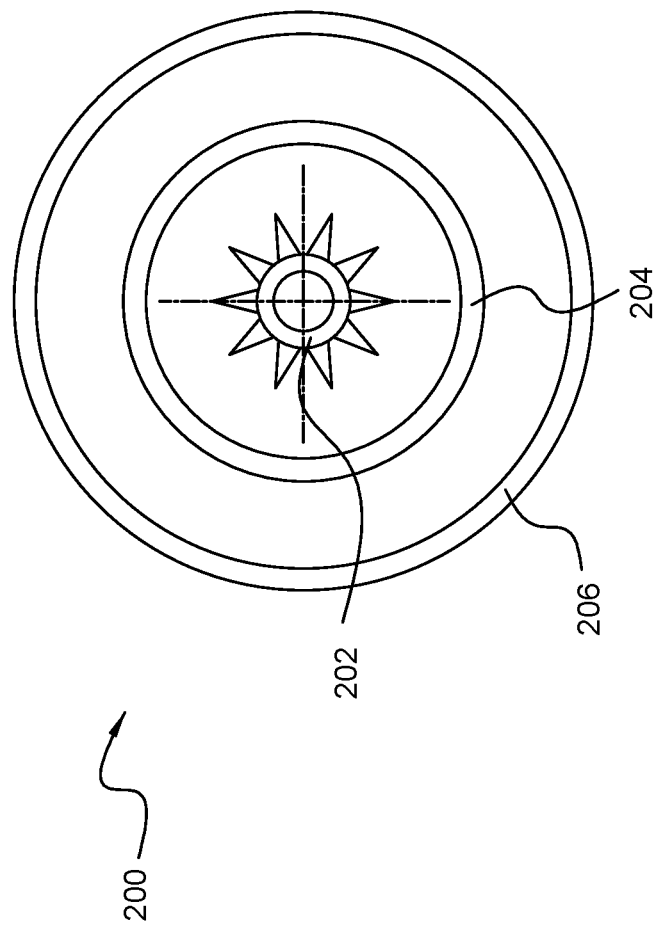
Figure 3A:
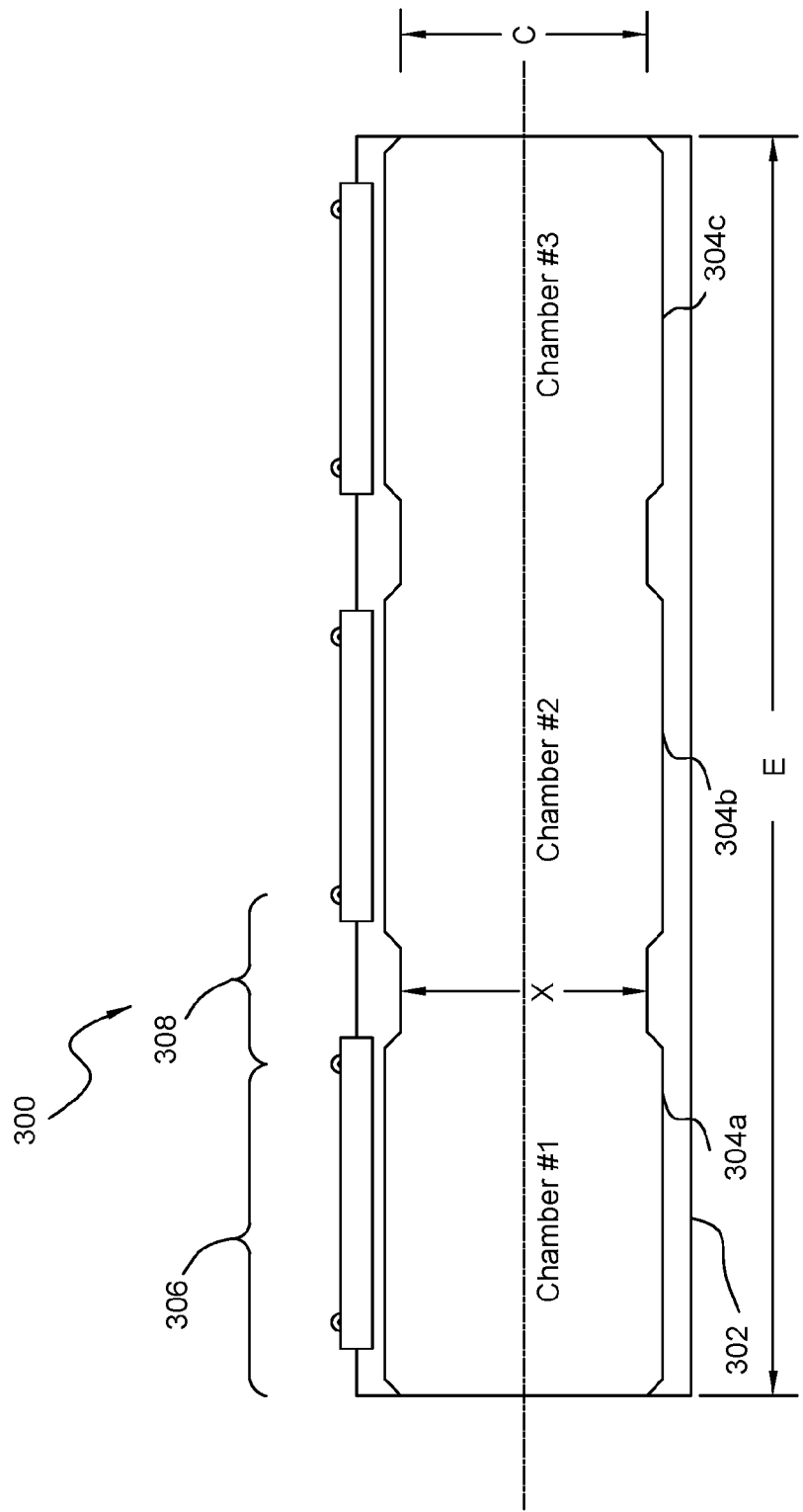
Figure 3B:
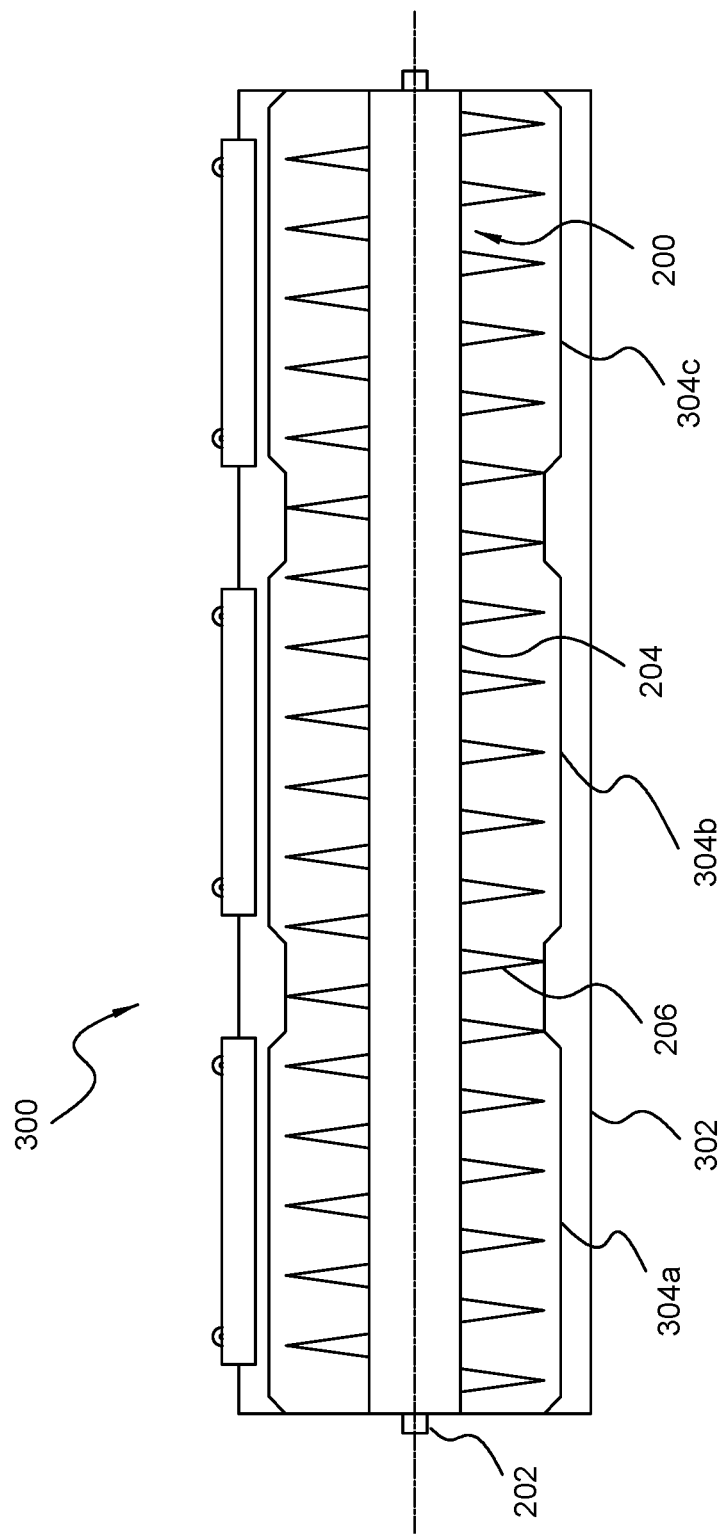

Having thus described the invention in general terms, reference will now be made to the accompanying drawings, which are not necessarily drawn to scale, and wherein:

FIG. 1A illustrates a perspective view of an apparatus for thermal treatment of organic waste, in accordance with an embodiment of the present disclosure;

FIG. 1B illustrates a schematic view of the apparatus of FIG. 1A, in accordance with an embodiment of the present disclosure;

FIG. 1C illustrates a side view of the apparatus of FIG. 1B, in accordance with an embodiment of the present of the present disclosure;

FIG. 1D illustrates a part of the apparatus of FIG. 1A for a manual injection of dry steam, in accordance with an embodiment of the present disclosure;

FIG. 1E illustrates another part of the apparatus of FIG. 1A for ejection of dry steam from an auger, in accordance with an embodiment of the present disclosure;

FIG. 2A illustrates a perspective view of an auger, in accordance with an embodiment of the present disclosure;

FIG. 2B illustrates a part of the auger of FIG. 2A, in accordance with an embodiment of the present disclosure;

FIG. 2C illustrates a front view of the auger, in accordance with an embodiment of the present disclosure;

FIG. 2D illustrates a top view of the auger having holes in each of plurality of hollow walled blades, in accordance with an embodiment of the present disclosure;

FIG. 2E illustrates a top view of the auger without holes in each of plurality of hollow walled blades, in accordance with another embodiment of the present disclosure;

FIG. 3A illustrates a schematic view of an interior of double wall, in accordance with an embodiment of the present disclosure; and FIG. 3B illustrates the schematic view of the interior of the double wall having the auger, in accordance with an embodiment of the present disclosure.

It should be noted that the accompanying figures are intended to present illustrations of exemplary embodiments of the present disclosure. These figures are not intended to limit the scope of the present disclosure. It should also be noted that accompanying figures are not necessarily drawn to scale.

DETAILED DESCRIPTION

Reference will now be made in detail to selected embodiments of the present disclosure in conjunction with accompanying figures. The embodiments described herein are not intended to limit the scope of the disclosure, and the present disclosure should not be construed as limited to the embodiments described. This disclosure may be embodied in different forms without departing from the scope and spirit of the disclosure. It should be understood that the accompanying figures are intended and provided to illustrate embodiments of the disclosure described below and are not necessarily drawn to scale. In the drawings, like numbers refer to like elements throughout, and thicknesses and dimensions of some components may be exaggerated for providing better clarity and ease of understanding.

It should be noted that the terms "first", "second", and the like, herein do not denote any order, quantity, or importance, but rather are used to distinguish one element from another. Further, the terms "a" and "an" herein do not denote a limitation of quantity, but rather denote the presence of at least one of the referenced item.

FIG. 1A illustrates a perspective view of an apparatus 100 for thermal treatment of organic waste, in accordance with various embodiment of the present disclosure. The apparatus 100 is a mechanical machine configured to collect and thermally process a pre-defined amount of the organic waste. In general, the apparatus 100 is an industrial cooker designed to thermally cook the pre-defined amount of organic waste. The pre-defined amount of organic waste is cooked for removing moisture, odor, bacteria and volume reduction.

The apparatus 100 includes a double wall 102, a first dry steam inlet 104, a plurality of manual steam injectors 106a-106d, a feed material inlet 108, a motor 110 and a plurality of dry steam inlets 112a-112e. In addition, the apparatus 100 includes one or more condenser outlets 114, one or more bellow valves, a first leg 122a and a second leg 122b. The above mentioned parts of the apparatus 100 are designed and assembled to perform thermal treatment of the pre-defined amount of organic waste. A capacity to process the pre-defined amount of the organic waste is based on a material handling capacity of a plurality of chambers 116a-116e (as shown in FIG. 1B). In an embodiment of the present disclosure, the capacity of the apparatus 100 to process the pre-defined amount of the plurality of the organic waste is 350 tons per day. In another embodiment of the present disclosure, the capacity to process the pre-defined amount of the organic waste is 400 tons per day. In yet another embodiment of the present disclosure, the capacity to process the pre-defined amount of the organic waste is 800 tons per day.

Further, the apparatus 100 is substantially positioned along a longitudinal axis. The double wall 102 of the apparatus 100 is metal wall designed to encapsulate each of the plurality of chambers 116a-116e (as shown in FIG. 1B). The double wall 102 is made of a solid sheet metal. The solid sheet metal of the double wall 102 encapsulates a pre-defined amount of dry steam present in each of the plurality of chambers. In addition, the solid sheet metal of the double wall 102 is designed in a hollow cylindrical form. The hollow cylinder form of the double wall 102 has an axis overlapping with the longitudinal axis of the apparatus 100. Further, the double wall 102 of the hollow cylinder is made of a metal or an alloy. In an embodiment of the present disclosure, the metal used for construction of the double wall 102 is steel. In another embodiment of the present disclosure, the metal used for construction of the double wall 102 is galvanized iron. In yet another embodiment of the present disclosure, any suitable metal or alloy may be used for the construction of the double wall 102.

As shown in FIG. 1C, the double wall 102 of the apparatus 100 has a diameter (shown as C). In addition, the diameter (C) of the double wall 102 depends on the material handling capacity of the each of the plurality of chambers 116a-116e. In an embodiment of the present disclosure, the diameter (C) is 1032 millimeters for the capacity of 350 tons per day. In another embodiment of the present disclosure, the diameter (C) is 1202 millimeters for the capacity of 400 tons per day. In yet another embodiment of the present disclosure, the diameter (C) is 1345 millimeters for the capacity of 800 tons per day.

Further, the first dry steam inlet 104 is present adjacent to the double wall 102 of apparatus 100. Moreover, the first dry steam inlet 104 is attached to a hollow cylindrical tank. The hollow cylindrical tank is substantially present parallel to the longitudinal axis of the apparatus 100. In addition, the cylindrical tank is separated from the double wall 102 of the apparatus 100. Further, the hollow cylindrical tank is designed to collect the pre-defined amount of dry steam from the first dry steam inlet 104. The cylindrical tank is connected to a hollow tube of lower diameter. The hollow tube extends parallel and separated from the longitudinal axis of the apparatus 100. Furthermore, each of the plurality of manual steam injectors 106a-106d substantially joins the hollow tube and the double wall of the apparatus 100. Each of the plurality of manual steam injectors 106a-106d (as shown in FIG. 1D) includes a manually turning valve between a first opening connected to the hollow tube and a second opening connected to the double wall 102.

As shown in FIG. 1B, the plurality of chambers 116a-116e is encapsulated concentrically by the double wall 102. In addition, the manually turning valve may be adjusted for addition of the pre-determined amount of steam to the plurality of chambers 116a-116e. Furthermore, each of the plurality of manual steam injectors 106a-106d are connected mechanically to each of the plurality of steam chambers 116a-116e.

In addition, the first dry steam inlet 104 is designed to inject the pre-defined amount of dry steam to each of the plurality of chambers 116a-116e. The first dry steam inlet 104 is positioned adjacent to the surface of the double wall 102 on an axis perpendicular to the longitudinal axis of the plurality of chambers 116a-116e. The first steam inlet 104 is associated with a manual valve for control over injection of the pre-defined amount of dry steam inside each of the plurality of chambers 116a-116e.

The plurality of chambers 116a-116e is designed to receive the pre-defined amount of organic waste. Each of the plurality of chambers 116a-116e has a cylindrical hollow body. Each of the plurality of chambers 116a-116e is connected in succession for a continuous movement of the pre-defined amount of organic waste along the longitudinal axis. It may be noted that the double wall 102 encapsulates a number of chambers 116a-116e; however, those skilled in the art would appreciate that the double wall 102 may encapsulate any number of chambers connected in tandem. In an embodiment of the present disclosure, the number of chambers connected in tandem is 3. In another embodiment of the present disclosure, the number of chambers connected in tandem is more than 3. The number of chambers connected in succession depends on size and the capacity of apparatus 100.

Further, the plurality of chambers 116a-116e is characterized by a first end 101 and a second end 105 (As shown in FIG. 1B). In general, the first end 101 and the second end 105 are separated from each other by a length (shown as B) equal to sum of lengths of each of the plurality of chambers 116a-116e. In an embodiment of the present disclosure, the length (B) of the plurality of chambers 116a-116e is 9000 mm for the capacity of 350 tons per day and 400 tons per day. In another embodiment of the present disclosure, the length of the plurality of chambers 116a-116e is 12000 mm for the capacity of 800 tons per day.

In addition, the first end 101 of the plurality of chambers 116a-116e is free from any encapsulation of the double wall 102. Moreover, the feed material inlet 108 is attached at the first end 101 of the successive connection of each of the plurality of chambers 116a-116d. The feed material inlet 108 is designed to receive the pre-defined amount of organic waste inside the successive connection of each of the plurality of chambers 116a-116d. Further, the feed material inlet 108 has a feed inlet section aligned perpendicular to the longitudinal axis. The feed material inlet 108 has a feed discharge section aligned perpendicular to the longitudinal axis of the plurality of chambers 116a-116e. The feed discharge section is internally connected to a first chamber 116a of the plurality of chambers 116a-116e. In an embodiment of the present disclosure, the feed inlet section and the feed discharge section of the feed material inlet 108 has a rectangular cross-section. It may be noted that the feed material inlet 108 has a rectangular cross-section; however, those skilled in the art would appreciate that the feed inlet section and the feed discharge section of the feed material inlet 108 may have any cross section. The feed inlet section of the feed material inlet 108 is open vertically upwards.

Furthermore, a circular base at the first end 101 of the cylindrical hollow body of the first chamber 116a of the plurality of chambers 116a-116e is associated with the motor 110 (As shown in FIG. 1C and FIG. 1A). The motor 110 is an electric motor designed to rotate at a pre-defined speed. Moreover, the motor is 110 includes a motor shaft. The motor shaft is attached to an auger 200 (as shown in FIG. 2A). The motor shaft is positioned to rotate the auger at a pre-defined range of a speed of rotation. The auger 200 is present concentrically inside the hollow cylindrical body of the successively connected plurality of chambers 116a-116e. In addition, the auger 200 is mechanically connected to a second dry steam inlet 111. The second dry steam inlet 111 is designed to collect the pre-defined amount of dry steam inside a hollow shaft of the auger 200. In an embodiment of the present disclosure, the motor 110 is an alternating current motor. In another embodiment of the present disclosure, the motor 110 is a direct current motor. In addition, the motor 110 is connected through a motor controller. The motor controller directs electric power and provides regulated current to the motor 110. The regulated current determines a rate of rotation of the motor 110. In an embodiment of the present disclosure, the motor controller is a manual controller. In another embodiment of the present disclosure, the motor controller is an automatic controller.

Further, the surface of each of the successive connection of the plurality of chambers 116a-116e is associated with the plurality of dry steam inlets 112a-112e. Each of the plurality of dry steam inlets 112a-112e is attached mechanically to a hollow tube of a plurality of hollow tubes. The plurality of dry steam inlets 112a-112e are designed and positioned to inlet the pre-defined amount of dry steam to each of the plurality of chambers 116a-116e. Each of the plurality of dry steam inlets 112a-112e is positioned on the surface of the double wall 102 substantially parallel along the longitudinal axis of the plurality of chambers 116a-116e. The plurality of dry steam inlets 112a-112e is connected to the plurality of hollow tubes. Each of the plurality of hollow tubes has a pre-defined length. The pre-defined length of a first hollow tube of the plurality of hollow tubes is measured from the base of the first chamber 116a to a mid-point of the first chamber 116a.

In addition, each of the plurality of hollow pipes is connected to one or more bellow valves. The one or more bellow valves are designed and configured to remove collected cold steam. Each of the one or more bellow valves has a flow passage of generally a circular cross-section parallel substantially along the longitudinal axis. Moreover, a valve disc member is positioned in the flow passage. The valve disc member has an outer periphery adapted to close the flow passage. The flow passage is closed from rotation of the valve disc member to a position transverse to the longitudinal axis.

Furthermore, the collected cold steam from the plurality of hollow pipes is transferred to a steamer. In general, the steamer is a device for generation of the pre-defined amount of dry steam and reception of the collected cold steam. In an embodiment of the present disclosure, the steamer is present in vicinity of the apparatus 100. The double wall 102 of the apparatus 100 is associated with one or more condenser outlets 114. Each of the one or more condenser outlets 114 is positioned at bottom of the double wall. The cold steam and liquid from the pre-defined amount of organic waste is ejected from each of the plurality of chambers 116a-116e to the one or more condenser outlets 114. Moreover, the cold steam and the liquid from the pre-defined amount of organic waste are transferred back to the steamer through feeding pipes.

As shown in FIG. 1B and FIG. 1E, the apparatus 100 includes a cold steam outlet 118 mechanically connected to a corresponding circular base at the second end 105 of the plurality of chambers 116a-116e. The cold steam outlet 118 is positioned along an axis synchronized with the longitudinal axis of the plurality of chambers 116a-116e. Further, the cold steam outlet 118 is internally connected to the auger 200 (as shown in FIG. 2A). The cold steam outlet 118 transfers the cold steam present inside the auger 200 to feeding pipes. In addition, the feeding pipes transfer the cold steam from the auger 200 to the steamer.

As shown in FIG. 1B, the apparatus 100 includes a processed material outlet 120. The processed material outlet is substantially attached to a bottom of the plurality of chambers 116a-116e. In addition, the processed material outlet 120 faces downwards with an axis perpendicular to the longitudinal axis of the plurality of chambers 116a-116e. Moreover, the processed material outlet 120 is characterized by a processed material opening. The processed material opening has a rectangular cross section. However, the processed material opening of the processed material outlet 120 may have any cross-section. Further, the processed material outlet 120 is designed to eject the pre-defined amount of organic waste subjected to thermal treatment.

Further, the double wall 102 of the apparatus 100 that encapsulates the plurality of chambers stands on a metallic frame. The metallic frame includes a first leg 122a attached to the first end 101 of the plurality of chambers 116a-116e. Accordingly, the metallic frame includes a second leg 122b attached of the second end 105 of the plurality of chambers 116a-116e. In addition, the first leg 122a and the second leg 122b are separated by a leg separation (shown as E in FIG. 1B). The leg separation (E) is 4050 millimeters. Moreover, the each of the first leg 122a and the second leg 122b has an inter leg separation (shown as D in FIG. 1C). In an embodiment of the present disclosure, the inter leg separation (D) for the first leg 122a and the second leg 122b is 950 millimeters. In another embodiment of the present disclosure, the inter leg separation (D) for the first leg 122a and the second leg 122b is 1660 millimeters.

Further, the first leg 122a and the second leg 122b are metallic legs designed to support weight of the apparatus 100. In addition, the weight of the apparatus 100 depends on the material handling capacity of the plurality of chambers 116a-116e. In an embodiment of the present disclosure, the weight of the apparatus 100 is 10700 kilograms for the capacity of 350 tons per day. In another embodiment of the present disclosure, the weight of the apparatus 100 is 12680 kilograms for the capacity of 400 tons per day. In yet another embodiment of the present disclosure, the weight of the apparatus 100 is 17500 kilograms for the capacity of 800 tons per day. In addition, the first leg 122a and the second leg 122b provides balance to the apparatus 100 when the apparatus is subjected to various vibrational and shock forces.

Furthermore, the apparatus 100 has a height (shown as F in FIG. 1B), an apparatus length (shown as A in FIG. 1B) and an apparatus width (shown as G in FIG. 1C). In an embodiment of the present disclosure, the apparatus 100 has the height (F), the apparatus length (A) and the apparatus width (G) of 1412 millimeters, 9860 millimeters and 1190 respectively. In another embodiment of the present disclosure, the apparatus 100 has the height (F), the apparatus length (A) and the apparatus width (G) of 1580 millimeters, 9860 millimeters and 1360 millimeters respectively. In yet another embodiment of the present disclosure, the apparatus 100 has the height (F), the apparatus length (A) and the apparatus width (G) of 2457 millimeters, 13020 millimeters and 1850 millimeters respectively.

In addition, the motor 110 operating the auger 200 in the apparatus 100 consumes a pre-defined amount of power. In an embodiment of the present disclosure, the pre-defined amount of the power is 7.5 kilowatt for the capacity of 350 tons per day. In another embodiment of the present disclosure, the predefined amount of power is 11 kilowatt for the capacity of 400 tons per day. In yet another embodiment of the present disclosure, the pre-defined amount of power is 15 kilowatts for the capacity of 800 tons per day. Moreover, the plurality of manual steam injectors 106a-106d and the second steam inlet 111 inject the pre-defined amount of dry steam inside each of the plurality of chambers 116a-116e and the auger 200. Further, the pre-defined amount of dry steam is injected at a pre-determined operating pressure and a pre-determined temperature. The pre-determined pressure depends on the material handling capacity of the apparatus 100. In an embodiment of the present disclosure, the operating pressure of the pre-determined amount of dry steam is 6 Bar. It may be noted that the operating pressure is 6 Bar; however, those skilled in the art would appreciate that the pre-determined amount of steam may be injected at any desirable operating pressure.

FIG. 2A illustrates a perspective view of the auger 200, in accordance with an embodiment of the present disclosure. It may be noted that to explain the elements of FIG. 2A, references will be made to the elements of the FIG. 1A, FIG. 1B, FIG. 1C, FIG. 1D and FIG. 1E. The auger 200 is designed to collect the pre-defined amount of dry steam and thermally transfer the heat to the pre-defined amount of organic waste for sufficient thermal treatment. In addition, the auger 200 is an eccentric and a symmetric auger. Further, the perspective view of the auger 200 is positioned along the longitudinal axis. The longitudinal axis of the auger 200 is symmetrically positioned with the longitudinal axis of the plurality of chambers 116a-116e.

The auger 200 includes a cylindrical shaft 204 and a plurality of hollow walled blades 206 (as shown in FIG. 2B). In addition, each of the plurality of hollow walled blades 206 is mechanically attached to the cylindrical shaft 204. The cylindrical shaft 204 is a hollow shaft having a first distal end 201 and a second distal end 203. Accordingly, the cylindrical shaft 204 has a length (shown as E in FIG. 1B) measured between the first distal end 201 and the second distal end 203. In general, the length of the auger 200 is equal to a length of the plurality of chambers 116a-116e. In addition, the length of the auger 200 is equal to a length of the cylindrical shaft 204. In an embodiment of the present disclosure, the length of the cylindrical shaft 204 is 9000 millimeters for the capacity of 350 tons per day and 400 tons per day. In another embodiment of the present disclosure, the length of the cylindrical shaft 204 is 12000 millimeters for the capacity of 800 tons per day.

As shown in FIG. 2C, the auger 200 includes the motor shaft 202. The motor shaft 202 passes through a center of the hollow body of the cylindrical shaft 204. The motor shaft 202 extends from the center of the cylindrical shaft 204 to the motor 110. Further, the hollow body of the cylindrical shaft 204 is attached to the plurality of hollow walled blades 206.

Furthermore, each blade of the plurality of hollow walled blades 206 (as shown in FIG. 2B) has a progressively constant flighting thickness from the first distal end 201 to the second distal end 203 of the cylindrical shaft 204. In addition, the orientation of a first section of the blade is complementary to a second section of a juxtaposed, next, subsequent blade. Further, each blade of the plurality of hollow walled blades 206 has a progressively constant flight height. The progressively constant flight height is constant owing to a constant diameter of the cylindrical shaft 204 from the first distal end 201 to the second distal end 203 of the auger 200. Moreover, the plurality of hollow walled blades 206 has a progressively constant distance between each adjacent blade of the plurality of hollow walled blades 206. The progressively constant distance is constant from the first distal end 201 to the second distal end 203 of the cylindrical shaft 204.

In an embodiment of the present disclosure, each of the plurality of hollow walled blades of the auger 200 includes a plurality of holes 208a-208i (as shown in FIG. 2D). The cylindrical shaft 204 and plurality of hollow walled blades 206 are filled with the pre-defined amount of dry steam. Each of the plurality of holes 208a-208i is designed to transfers jets of the pre-defined amount of dry steam to the pre-defined amount of organic waste present in the plurality of chambers 116a-116e. The pre-defined amount of organic waste is fed to the first chamber 116a of the plurality of chambers 116a-116e through the feed material inlet 108.

Further, the auger 200 is mechanically connected to the second dry steam inlet 111 (as shown in FIG. 1A) for a collection of the pre-defined amount of dry steam inside the cylindrical shaft 204. The second dry steam inlet 111 is placed on a cross-sectional surface at the first distal end 201 of the auger 200. The second dry steam inlet 111 is associated with an inlet valve for a control of the injection of the pre-defined amount of dry steam inside the hollow shaft of the auger 200. Further, the jets of the pre-defined amount of dry steam from the plurality of holes 208a-208i thermally cook the pre-defined amount of organic waste with shocks. In addition, the pre-determined amount of the organic waste is thermally cooked at a pre-determined temperature. In an embodiment of the present disclosure, the pre-determined temperature is 200° C. In another embodiment of the present disclosure, the pre-determined temperature is more or less than 200° C.

In addition, the thermal treatment of the pre-defined amount of organic waste in the first chamber 116a thermally removes the bad odor and bacteria. In addition, the pre-defined amount of organic waste is rendered dry with a pre-defined amount of water. The pre-defined amount of organic waste continues to travel through subsequent chambers 116b-116e of the plurality of chambers 116a-116e. The subsequent chambers 116b-116e chambers create in-direct heat in order to condense, cook, and bring the pre-defined amount of organic waste to same temperature. The subsequent chambers 116b-116e creates pressure as the pre-defined amount of organic waste moves from the first distal end 201 to the second distal end 203.

In another embodiment of the present disclosure, each of the plurality of hollow walled blades of the auger 200 has no holes (as shown in FIG. 2E). Further, the pre-determined amount of steam heats surface of the cylindrical shaft 204 and walls of each of the plurality of hollow walled blades 206. Further, heat from the surface of the cylindrical shaft 204 and the walls of each of the plurality of hollow walled blades 206 is transferred conductively to the pre-defined amount of organic waste present inside the plurality of chambers 116a-116e. Further, the cylindrical shaft 204 and the plurality of hollow walled blades 206 traverse from the first distal end 201 to the second distal end 205 along the longitudinal axis. The cylindrical hollow body of each of the plurality of chambers 116a-116e creates pressure for the pre-defined amount of organic waste that moves forward with the auger 200.

Furthermore, the auger 200 is associated with the cold steam outlet 118 (as shown in FIG. 1E). The cold steam outlet 118 collects the cold steam from the cylindrical shaft of the auger 200. The cold steam outlet 118 is placed at the second distal end of the auger. The cold steam outlet 118 is associated with an outlet valve for the controlled ejection of the cold steam outside the hollow shaft of the auger 200.

FIG. 3A illustrates a schematic view 300 of an interior of a double wall 302, in accordance with an embodiment of the present disclosure. The plurality of chambers 304a-304c (also shown as the plurality of chambers 116a-116e in FIG. 1B) is designed to collect the pre-defined amount of the plurality of organic waste from the feed material inlet 108. In addition, each of the plurality of chambers 304a-304c is designed to receive the pre-defined amount of dry steam from the plurality of manual steam injectors 106a-106d (as explained above in detailed description of FIG. 1A, FIG. 1B and FIG. 1D).

In general, each of the plurality of chambers 304a-304c is successively connected to each other. Each chamber of the plurality of chambers 304a-304c has the cylindrical hollow body. Moreover, the cylindrical hollow body has a first diameter (shown as C) of a first section 306 and a second diameter (shown as X) of a second section 308. Each of the plurality of chambers 304a-304c is connected in the succession for the continuous movement of the pre-defined amount of organic waste along the longitudinal axis. In addition, the second diameter (X) of the second section 308 is less than the first diameter (C) of the first section 306. In an embodiment of the present disclosure, the first diameter of the first section of each of the plurality of chambers 100 is 1032 millimeters. In another embodiment of the present disclosure, the first diameter (C) of the first section 306 of each of the plurality of chambers 100 is 1202 millimeters. In yet another embodiment of the present disclosure, the first diameter (C) of the first section 308 of each of the plurality of chambers 100 is 1345 millimeters.

As shown in FIG. 3B, the auger 200 is present concentrically along the longitudinal axis of the double wall 302. In addition, the auger 200 is present inside the plurality of chambers 304a-304c (as explained above in the detailed description of FIG. 2A, FIG. 2B, FIG. 2C, FIG. 2D and FIG. 2E).

Further, the present apparatus has several advantages over the prior art. The present apparatus provides a compact and sophisticated thermal treatment device with an increased processing efficiency. Further, the apparatus derives a lower power with an increased output. Thus, the apparatus provides a higher return of investment and an easier finance of resources. Furthermore, the use of the apparatus has a various ecological benefits. In conventional thermal treatment units, the material is not processed to an extent that the bad odor and bacterial get killed. The apparatus of the invention overcomes this disadvantage. The apparatus kills the bacteria and the odor in first chamber of the plurality of chambers. In addition, the apparatus reduces the size of the organic waste from coarse to a finer and homogeneous blend. This decreases the overall volume of the organic waste initially fed inside the apparatus significantly. In addition, the apparatus reduces the water content from the organic waste and helps in further decomposition of organic waste without bad odor. In addition, the apparatus provides a solution to the growing problem of large scale waste dumping. The processed waste occupies lower area, negligible bad odor and negligible bacteria.

The foregoing descriptions of specific embodiments of the present technology have been presented for purposes of illustration and description. They are not intended to be exhaustive or to limit the present technology to the precise forms disclosed, and obviously many modifications and variations are possible in light of the above teaching. The embodiments were chosen and described in order to best explain the principles of the present technology and its practical application, to thereby enable others skilled in the art to best utilize the present technology and various embodiments with various modifications as are suited to the particular use contemplated. It is understood that various omissions and substitutions of equivalents are contemplated as circumstance may suggest or render expedient, but such are intended to cover the application or implementation without departing from the spirit or scope of the claims of the present technology.

While several possible embodiments of the invention have been described above and illustrated in some cases, it should be interpreted and understood as to have been presented only by way of illustration and example, but not by limitation. Thus, the breadth and scope of a preferred embodiment should not be limited by any of the above-described exemplary embodiments.

What is claimed is:

1. An apparatus for thermal treatment of a pre-defined amount of organic waste, said apparatus comprising:
   a plurality of chambers for receiving said pre-defined amount of organic waste, wherein each of said plurality of chambers has a cylindrical hollow body having a first diameter of a first section and a second diameter of a second section, wherein each of said plurality of chambers being connected in succession for a continuous movement of said pre-defined amount of organic waste along a longitudinal axis, wherein said second diameter is less than said first diameter, said plurality of chambers generating pressure as the pre-defined amount of organic waste is moved from a chamber of the plurality of chambers to a next chamber of the plurality of chambers, the plurality of chambers comprising:
      a feed material inlet attached at a first end of said plurality of chambers; and
      a processed material outlet attached to at a second end of said plurality of chambers;
   a double wall encapsulating each of said plurality of chambers; and
   an auger accommodated within said cylindrical hollow body of each of said plurality of chambers, wherein said auger being positioned parallel to said longitudinal axis of each of said plurality of chambers for moving forward the pre-defined amount of organic waste and wherein said auger comprising:
      a cylindrical shaft being a hollow shaft having a first distal end and a second distal end;
      a motor shaft for rotating said auger inside said plurality of chambers;
      an auger dry steam inlet for collecting a pre-defined amount of dry steam inside said hollow shaft of said auger
      the auger dry steam inlet is associated with an inlet valve for a control of injection of the pre-defined amount of dry steam inside the hollow shaft of the auger at the first distal end;
      a cold steam outlet for collecting cold steam inside from said cylindrical shaft of said auger at the second distal end; and
      a plurality of hollow walled blades with no holes;
      the pre-determined amount of steam within hollow shaft of the auger heats surface of the cylindrical shaft and walls of each of the plurality of hollow walled blades;
      the heat from the surface of the cylindrical shaft and the walls of each of the plurality of hollow walled blades is transferred conductively to the pre-defined amount of organic waste present inside the plurality of chambers;
      the plurality of hollow walled blades having a constant flighting thickness from said first distal end to said second distal end of said cylindrical shaft, with orientation of a first section of a fighting complementary to a second section of a juxtaposed, next, subsequent flighting, wherein said plurality of hollow walled blades having a constant flight height, wherein said constant flight height being constant due to a constant diameter of said cylindrical shaft from said first distal end to said second distal end of said auger, wherein said plurality of hollow walled blades having constant distance between each of said plurality of hollow walled blades, wherein said constant distance being constant from said first distal end to said second distal end.

2. The apparatus as recited in claim 1, further comprising a first dry steam inlet for injecting said pre-defined amount of dry steam to each of said plurality of chambers and said auger, wherein said first dry steam inlet being positioned adjacent to a surface of said double wall on an axis perpendicular to said longitudinal axis of said plurality of chambers, wherein said first steam inlet being associated with a manual valve for controlling injection of said pre-defined amount of dry steam inside each of said plurality of chambers and said auger.

3. The apparatus as recited in claim 1, further comprising a plurality of dry steam inlets positioned on said surface of said double wall for inletting said pre-defined amount of dry steam to said surface of said double wall substantially parallel along said longitudinal axis of said plurality of chambers, wherein said plurality of dry steam inlets being connected to a steam source via hollow tubes.

4. The apparatus as recited in claim 1, further comprising one or more bellow valves for removing a collected cold steam, wherein each of said one or more bellow valves having a flow passage of generally a circular cross-section parallel substantially along said longitudinal axis, wherein a valve disc member positioned in said passage and having an outer periphery adapted to close said passage when rotated to a position generally transverse to said longitudinal axis.

5. The apparatus as recited in claim 1, wherein said auger further comprises a motor connected to said motor shaft for rotation of said cylindrical shaft and said plurality of hollow walled blades, wherein said motor shaft having an interlocking element substantially aligned along said longitudinal axis of said auger, wherein said motor shaft interlocks at said second distal end of said cylindrical shaft of said auger.

6. The apparatus as recited in claim 5, wherein said motor rotates said auger at a pre-defined range of a speed of rotation.

7. The apparatus as recited in claim 1, wherein said cold steam outlet being placed on a cross-sectional surface at said second distal end of said auger, wherein said cold steam outlet being associated with an outlet valve for controlling an ejection of said cold steam outside said hollow shaft of said auger.

8. The apparatus as recited in claim 1, wherein the auger dry steam inlet being placed on a cross-sectional surface at said first distal end of said auger, wherein said auger dry steam inlet being associated with an inlet valve for controlling an injection of said pre-defined amount of dry steam inside said hollow shaft of said auger.

9. The apparatus as recited in claim 1, wherein said feed material inlet having a feed inlet section aligned perpendicular to said longitudinal axis, wherein said feed material inlet having a feed discharge section aligned perpendicular to said longitudinal axis of said plurality of chambers, and wherein said feed discharge section internally connected to a first chamber of said plurality of chambers.

10. The apparatus as recited in claim 1, wherein said auger being an eccentric auger and symmetric auger and wherein said cylindrical shaft of said auger has a length measured between said first distal length and said second distal length.

11. The apparatus as recited in claim 1, wherein said pre-determined amount of organic waste being thermally treated at a pre-determined temperature in a first chamber of said plurality of chambers.

12. The apparatus as recited in claim 1, wherein said cylindrical shaft and said plurality of hollow walled blades being filled with said pre-defined amount of dry steam.

13. The apparatus as recited in claim 1, wherein said cylindrical shaft and said plurality of hollow walled blades being filled with said pre-defined amount of dry steam, wherein an outer surface of said cylindrical shaft and said plurality of hollow walled blades being transferring thermal energy to said pre-defined amount of organic waste through dissipation.

14. The apparatus as recited in claim 1, wherein said cylindrical shaft and said plurality of hollow walled blades being traversing from said first distal end to said second distal end along said longitudinal axis and wherein said cylindrical hollow body of each of said plurality of chambers creates pressure for said pre-defined amount of organic waste moving forward with said auger.

15. The apparatus as recited in claim 1, wherein a cold steam collected from a cold steam outlet of said auger being fed back to a steamer for regeneration of said pre-defined amount of dry steam.

16. An apparatus for thermal treatment of a pre-defined amount of organic waste, said apparatus comprising:
a plurality of chambers for receiving said pre-defined amount of organic waste, wherein each of said plurality of chambers has a cylindrical hollow body having a first diameter of a first section and a second diameter of a second section, wherein each of said plurality of chambers being connected in succession for a continuous movement of said pre-defined amount of organic waste along a longitudinal axis, wherein said second diameter is less than said first diameter, said plurality of chambers generating pressure as the pre-defined amount of organic waste is moved from a chamber of the plurality of chambers to a next chamber of the plurality of chambers, the plurality of chambers comprising:
a feed material inlet attached at a first end of said plurality of chambers; and
a processed material outlet attached to at a second end of said plurality of chambers;
a double wall encapsulating each of said plurality of chambers; and
an auger accommodated within a cylindrical hollow body of each of said plurality of chambers for moving forward the predefined amount of organic waste, wherein said auger being filled with pre-defined amount of dry steam, wherein said auger comprising:
a cylindrical shaft being a hollow shaft having a first distal end and a second distal end;
a motor shaft for rotating said auger inside said plurality of chambers,
an auger dry steam inlet for collecting said pre-defined amount of dry steam inside said hollow shaft of said auger; and
a plurality of hollow walled blades with no holes;
the auger dry steam inlet is associated with an inlet valve for a control of injection of the pre-defined amount of dry steam inside the hollow shaft of the auger at the first distal end of the auger;

a cold steam outlet for collecting cold steam inside from said cylindrical shaft of said auger at the second distal end of the auger;

the pre-determined amount of steam within hollow shaft of the auger heats surface of the cylindrical shaft and walls of each of the plurality of hollow walled blades;

the heat from the surface of the cylindrical shaft and the walls of each of the plurality of hollow walled blades is transferred conductively to the pre-defined amount of organic waste present inside the plurality of chambers;

the plurality of hollow walled blades having a constant flighting thickness from said first distal end to said second distal end of said cylindrical shaft, with orientation of a first section of a fighting complementary to a second section of a juxtaposed, next, subsequent flighting, wherein said plurality of hollow walled blades having a constant flight height, wherein said constant flight height being constant due to a constant diameter of said cylindrical shaft from said first distal end to said second distal end of said auger, wherein said plurality of hollow walled blades having constant distance between each of said plurality of hollow walled blades, wherein said constant distance being constant from said first distal end to said second distal end.

17. The apparatus as recited in claim 16, further comprising a first dry steam inlet for injecting said pre-defined amount of dry steam to each of said plurality of chambers and said auger, wherein said first dry steam inlet being positioned adjacent to a surface of said double wall on an axis perpendicular to said longitudinal axis of said plurality of chambers, wherein said first steam inlet being associated with a manual valve for controlling injection of said pre-defined amount of dry steam inside each of said plurality of chambers and said auger.

18. The apparatus as recited in claim 16, further comprising a plurality of dry steam inlets for inletting said pre-defined amount of dry steam to each of said plurality of chambers, wherein each of said plurality of dry steam inlets being positioned on said surface of said double wall substantially parallel along said longitudinal axis of said plurality of chambers, wherein said plurality of dry steam inlets being connected to a steam source via a set of hollow tubes.

19. The apparatus as recited in claim 16, further comprising one or more bellow valves for removing a collected cold steam, wherein each of said one or more bellow valves having a flow passage of generally a circular cross-section parallel substantially along said longitudinal axis, wherein a valve disc member positioned in said passage and having an outer periphery adapted to close said passage when rotated to a position generally transverse to said longitudinal axis.

20. The apparatus as recited in claim 16, wherein said auger further comprises a cold steam outlet for collecting cold steam inside from said cylindrical shaft of said auger, wherein said cold steam outlet being placed on a cross-sectional surface at said second distal end of said auger, wherein said cold steam outlet being associated with an outlet valve for controlling an ejection of said cold steam out of said hollow shaft of said auger.

* * * * *